United States Patent
Yamazaki et al.

(10) Patent No.: US 10,478,784 B2
(45) Date of Patent: Nov. 19, 2019

(54) DEVICE AND METHOD FOR OBSERVING AND FILTER FOR CAPTURING A MINUTE SUBSTANCE

(71) Applicant: AGC Inc., Chiyoda-ku (JP)

(72) Inventors: Shuji Yamazaki, Chiyoda-ku (JP); Shuichiro Kimura, Chiyoda-ku (JP); Kenji Kitaoka, Chiyoda-ku (JP); Yu Hanawa, Chiyoda-ku (JP)

(73) Assignee: AGC Inc., Chiyoda-ku (JP)

(*) Notice: Subject to any disclaimer, the term of this patent is extended or adjusted under 35 U.S.C. 154(b) by 36 days.

(21) Appl. No.: 15/682,715

(22) Filed: Aug. 22, 2017

(65) Prior Publication Data

US 2017/0348647 A1  Dec. 7, 2017

Related U.S. Application Data

(63) Continuation of application No. PCT/JP2016/055913, filed on Feb. 26, 2016.

(30) Foreign Application Priority Data

Feb. 26, 2015 (JP) ................................. 2015-036425

(51) Int. Cl.
 *B01D 71/04* (2006.01)
 *C03C 11/00* (2006.01)
 (Continued)

(52) U.S. Cl.
 CPC ............. *B01D 71/04* (2013.01); *B01D 69/02* (2013.01); *C03C 3/089* (2013.01); *C03C 11/00* (2013.01);
 (Continued)

(58) Field of Classification Search
 CPC ...... B01D 71/04; B01D 69/02; G01N 1/4077; G01N 1/10; C03C 11/005; C03C 3/089; C03C 11/00; G02B 21/34
 See application file for complete search history.

(56) References Cited

U.S. PATENT DOCUMENTS

| 5,234,594 A | 8/1993 | Tonucci et al. |
| 5,306,661 A * | 4/1994 | Tonucci ................. B82Y 10/00 148/DIG. 50 |

(Continued)

FOREIGN PATENT DOCUMENTS

| CA | 2 583 469 A1 | 1/2007 |
| CN | 101039798 A | 9/2007 |

(Continued)

OTHER PUBLICATIONS

International Search Report dated May 24, 2016 in PCT/JP2016/055913, filed on Feb. 26, 2016 (with English Translation).

(Continued)

*Primary Examiner* — Chester T Barry
(74) *Attorney, Agent, or Firm* — Oblon, McClelland, Maier & Neustadt, L.L.P.

(57) ABSTRACT

There is provided a glass substrate for observing minute substance, made of porous glass and capable of separating and capturing a minute substance with a 10 to 500 nm average particle diameter contained in a solution or a suspension, comprising a porous glass substrate having a plurality of pores, wherein the plurality of pores has an average pore diameter ranging from 30 to 110% of the average particle diameter of the minute substance, each of the plurality of pores has a surface pore diameter on an uppermost surface of the glass substrate, a standard deviation of the surface pore diameter is 60% or less of the average particle diameter of the minute substance, and a pore with a pore diameter ranging from 60 to 140% of a pore (Continued)

diameter at peak top in a pore diameter distribution of the plurality of pores occupies 90% or more of total pore volume.

11 Claims, 1 Drawing Sheet

(51) Int. Cl.

| | |
|---|---|
| *G01N 1/10* | (2006.01) |
| *G02B 21/34* | (2006.01) |
| *B01D 69/02* | (2006.01) |
| *C03C 3/089* | (2006.01) |
| *G01N 1/40* | (2006.01) |
| *G02B 21/00* | (2006.01) |

(52) U.S. Cl.
CPC .............. *C03C 11/005* (2013.01); *G01N 1/10* (2013.01); *G01N 1/4077* (2013.01); *G02B 21/34* (2013.01); *G01N 2001/4088* (2013.01); *G02B 21/0076* (2013.01)

(56) References Cited

U.S. PATENT DOCUMENTS

| | | | |
|---|---|---|---|
| 2004/0248144 A1* | 12/2004 | Mir | C12Q 1/6818 435/6.11 |
| 2010/0323573 A1 | 12/2010 | Chu et al. | |
| 2012/0231970 A1 | 9/2012 | Nakagama et al. | |

FOREIGN PATENT DOCUMENTS

| | | |
|---|---|---|
| GB | 2 284 362 A | 6/1995 |
| JP | 62-501678 | 7/1987 |
| JP | 5-222091 | 8/1993 |
| JP | 8-502200 | 3/1996 |
| JP | 2001-232163 | 8/2001 |
| JP | 2003-139704 | 5/2003 |
| JP | 2008-515668 | 5/2008 |
| JP | 2010-195612 | 9/2010 |
| WO | WO 86/04088 A1 | 7/1986 |
| WO | WO 93/25301 A1 | 12/1993 |
| WO | WO 2007/001405 A2 | 1/2007 |
| WO | WO 2011/040525 A1 | 4/2011 |
| WO | WO 2014/192919 A1 | 12/2014 |

OTHER PUBLICATIONS

Written Opinion dated May 24, 2016 in PCT/JP2016/055913, filed on Feb. 26, 2016.

* cited by examiner

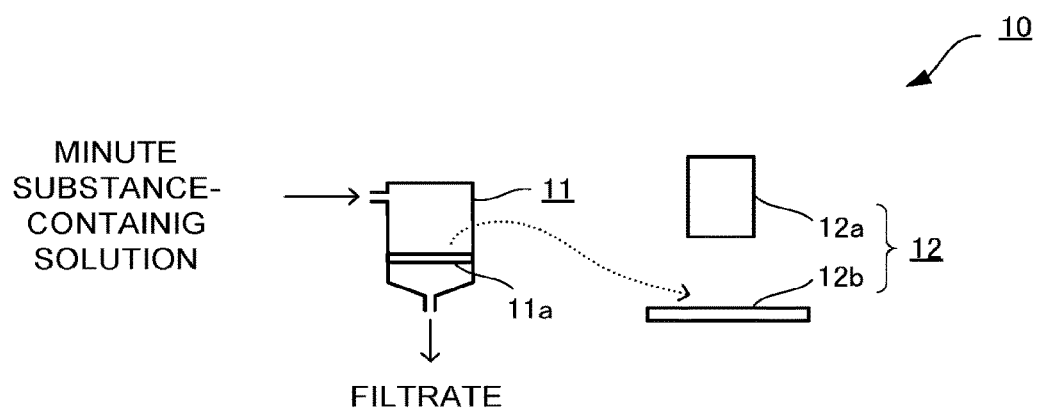

DEVICE AND METHOD FOR OBSERVING
AND FILTER FOR CAPTURING A MINUTE
SUBSTANCE

CROSS-REFERENCE TO RELATED APPLICATIONS

This application is a continuation of prior International Application No. PCT/JP2016/055913 filed on Feb. 26, 2016 which is based upon and claims the benefit of priority from Japanese Patent Application No. 2015-036425 filed on Feb. 26, 2015; the entire contents of all of which are incorporated herein by reference.

FIELD

The present invention relates to a filter for capturing minute substance capable of separating and capturing a minute substance, a glass substrate for observing minute substance, a minute substance observation device including the glass substrate for observing minute substance, a minute substance capturing method, and a minute substance observation method.

BACKGROUND

As a technique to separate a solid substance contained in a solution or a suspension from liquid, filtration with a filter has been conventionally known. As the filter used for the filtration, filters whose pore diameters differ depending on their intended use have been known. As a filter capable of separating and capturing a minute substance whose average particle diameter is 500 nm or less, those of resin have been conventionally in general use. However, it is difficult to improve capturing efficiency of a minute substance being a substance to be captured to a certain level or more.

Further, it is known that porous glass having a nano-order pore diameter is usable as a gas separation membrane (JP-A 2010-195612). To obtain this porous glass, glass is phase-separated and thereafter parts of its components are eluted by acid treatment. This Reference, however, gives no description regarding the separation of a minute substance contained in a solution or a suspension.

SUMMARY

If a captured minute substance can be observed as it is on a filter, troubles, cost, and the like in the analysis of the minute substance can be reduced, which is desirable.

It is an object of the present invention to provide a filter for capturing a minute substance capable of separating and capturing a minute substance in a solution or a suspension and a minute substance capturing method using the filter for capturing a minute substance. Another object of the present invention is to provide a glass substrate for observing minute substance on whose surface a minute substance can be directly observed, a minute substance observation device including the glass substrate for observing minute substance, and a minute substance observation method.

A filter for capturing a minute substance of the present invention is a minute substance capturing filter made of a porous glass substrate having a plurality of pores, wherein the plurality of pores has an average pore diameter ranging from 5 to 2500 nm and a pore diameter ranging from 60 to 140% of a pore diameter at peak top in a pore diameter distribution of the plurality of pores occupies 90% or more of total pore volume of the plurality of pores.

A glass substrate for observing minute substance of the present invention is a minute substance observation glass substrate made of porous glass and capable of separating and capturing a minute substance with a 10 to 500 nm average particle diameter contained in a solution or a suspension, comprising a porous glass substrate having a plurality of pores, wherein the plurality of pores has an average pore diameter ranging from 30 to 110% of the average particle diameter of the minute substance, each of the plurality of pores has a surface pore diameter on a main surface of the porous glass substrate, a standard deviation of the surface pore diameter on an uppermost surface of the glass substrate is 60% or less of the average particle diameter of the minute substance, a pore with a pore diameter ranging from 60 to 140% of a pore diameter at peak top in a pore diameter distribution of the plurality of pores occupies 90% or more of total pore volume of the plurality of pores.

A minute substance observation device of the present invention includes: a capturing unit including the above-described glass substrate for observing minute substance and being capable of separating and capturing a minute substance with a 10 to 500 nm average particle diameter contained in a solution or a suspension; and an observing unit for observing the minute substance captured on a surface of the glass substrate.

A minute substance capturing method of the present invention includes: introducing the solution or a suspension containing a minute substance with a 10 to 500 nm average particle diameter to a porous glass substrate having a plurality of pores, and separating and capturing the minute substance by the glass substrate, wherein the plurality of pores has an average pore diameter ranging from 30 to 500% of the average particle diameter of the minute substance, and a pore diameter ranging from 60 to 140% of a pore diameter at peak top in a pore diameter distribution of the plurality of pores occupies 90% or more of total pore volume of the plurality of pores.

A minute substance observation method of the present invention includes: separating and capturing a minute substance with a 10 to 500 nm average particle diameter by the aforesaid glass substrate for observing minute substance, from a solution or a suspension containing the minute substance; and observing the minute substance captured on a surface of the glass substrate for observing minute substance.

According to the filter for capturing a minute substance and the minute substance capturing method of the present invention, it is possible to efficiently separate and capture a minute substance in a solution or a suspension. Further, according to the glass substrate for observing minute substance, the minute substance observation device, and the minute substance observation method, it is possible to observe the captured minute substance as it is on the glass substrate with an optical microscope. This enables the efficient observation, inspection, and the like of the minute substance with a simple operation.

BRIEF DESCRIPTION OF THE DRAWINGS

FIG. 1 is a view illustrating the schematic structure of a minute substance observation device of the present invention.

DETAILED DESCRIPTION

Hereinafter, a filter for capturing a minute substance, a minute substance capturing method, a glass substrate for observing minute substance, a minute substance observation device, and a minute substance observation method of the present invention will be described in detail.

[Minute Substance Capturing Filter]

The filter for capturing a minute substance of the present invention is a glass substrate capable of separating and capturing a minute substance with a 10 to 500 nm average particle diameter contained in a solution or a suspension. The filter for capturing a minute substance is made of porous glass having many pores so as to be capable of the solid-liquid separation of the minute substance and liquid.

The average particle diameter of the minute substance which is a substance to be captured in the present invention is 10 to 500 nm, and preferably 50 to 150 nm. In the present specification, the average particle diameter of the minute substance is a 50% integrated value ($D_{50}$) found from a volume-based particle diameter distribution measured by a laser diffraction/scattering method or microscope observation. Examples of the minute substance include asbestos, carbon black, ink, colloidal particles, virus, and biomolecules such as albumin, antibody, and exosome. In recent years, extracellular vesicles such as exosome have been drawing attention because it has been found out that they can be used for the diagnosis of illness such as cancer.

Here, an average pore diameter of the pores that the filter for capturing a minute substance has is 5 to 2500 nm, preferably 5 to 550 nm, more preferably 10 to 300 nm, still more preferably 20 to 200 nm, and especially preferably 50 to 150 nm. The average pore diameter here refers to a pore diameter at peak top which is determined based on a pore diameter distribution found by a BHJ method from a nitrogen adsorption isotherm by a gas adsorption method.

The average pore diameter is preferably within a range of 30 to 500% of the average particle diameter of the minute substance which is the substance to be separated and captured (that is, its ratio to the average particle diameter of the minute substance as a reference (100%) is preferably within a range of 30 to 500%). This ratio is more preferably 50 to 110%, and still more preferably 60 to 100%. By setting the average pore diameter to 500% or less of the average particle diameter of the minute substance (five times or less of the average particle diameter), it is possible to capture the minute substance on the capturing filter or in the pores. Further, by setting the average pore diameter to 110% or less of the average particle diameter of the minute substance (1.1 times or less of the average particle diameter), it is possible to surely capture the minute substance on the capturing filter. Further, by setting the average pore diameter to more than 30% of the average particle diameter of the minute substance, it is possible to reduce a pressure loss to efficiently separate the minute substance owing to the absence of excessively small pore diameter. It is also possible to pass a substance whose average particle diameter is excessively smaller than that of the target minute substance and capture only the target minute substance.

90% or more of total pore volume of the pores in the filter for capturing a minute substance have pore diameters within a range of 60 to 140% of the pore diameter at peak top in the pore diameter distribution (that is, ratios of their pore diameters to the pore diameter at peak top as a reference (100%) are within a range of 60 to 140%). In other words, their pore diameters fall within ±40% when the pore diameter at peak top is set as a reference (0%) (note that the reference used for the calculation of the ratio at this time is the pore diameter at peak top similarly to the above). Since a distribution width of the pore diameter distribution is narrow, it is possible to separate and capture the minute substance stably and efficiently. More preferably, 95% or more of the aforesaid pores have pore diameters within the range of 60 to 140% of the pore diameter at peak top in the pore diameter distribution.

The porosity of the filter for capturing a minute substance is preferably 20 to 90 vol %, more preferably 30 to 80 vol %, and especially preferably 40 to 70 vol % in view of preventing an excessive decrease of strength. Note that, in the present specification, the porosity is a value calculated from the apparent density and the true density of the glass substrate. The apparent density and the true density are found by a pycnometer method.

Since the filter for capturing a minute substance is a porous body as described above, the findings on a conventionally known glass filter cannot be applied as it is regarding whether or not it can be stably used for the solid-liquid separation of a solution or a suspension. As a result of studies on a condition under which the aforesaid glass substrate having the specific pores is capable of stably and surely performing the solid-liquid separation, the present inventors have found out that setting a ratio between a ratio of the area of a main surface to the plate thickness of the filter for capturing a minute substance and the average pore diameter (area/plate thickness/$Log_{10}$ (average pore diameter)) to a predetermined relation is effective.

Specifically, in the filter for capturing a minute substance of the present invention, the ratio between the ratio of the area of the main surface to the plate thickness and the average pore diameter (area (cm$^2$)/plate thickness (mm)/$Log_{10}$ (average pore diameter (nm))) is preferably 4.5 cm$^2$/mm or less, more preferably within a range of 0.01 to 2.5 cm$^2$/mm, and especially preferably within a range of 0.01 to 2 cm$^2$/mm. The filter for capturing a minute substance satisfying this relation has resistance against a high pressure at the time of the separation and capturing of the minute substance in the solution or the suspension. Moreover, satisfying this relation enables a significant reduction of the occurrence of a warp of the filter even if the plate thickness is as thin as 0.5 mm or less. Further, reducing the plate thickness is preferable because this can reduce a pressure loss at the time of the separation and capturing. The above relation can be represented by the following formula (1), $$\frac{S}{D \cdot \log_{10} d} \leq 4.5 [\text{cm}^2/\text{mm}] \qquad (1)$$

where S [cm$^2$] is an area of main surface to a plate thickness of the glass substrate, D [mm] is a plate thickness of the porous glass substrate, and d [nm] is the average pore diameter.

The thickness of the filter for capturing a minute substance is preferably 0.1 to 5 mm, and more preferably 0.1 to 1 mm. The area of the filter for capturing a minute substance is preferably 0.1 to 10.5 cm$^2$, more preferably 0.2 to 6 cm$^2$, and especially preferably 0.3 to 6 cm$^2$. The shape of the filter is not limited as long as it has a plate shape, and its shape in a plane view may be any of various shapes, for example, a polygon such as a triangle or a square, or a circle such as a perfect circle or an ellipse. Among them, the circle, in particular, the perfect circle is preferable for the separation and capturing of the minute substance in the solution or the suspension because a load from a liquid component is applied uniformly to the filter in this shape, leading to high strength.

The glass forming the filter for capturing minute substance is not limited as long as it has the aforesaid characteristics. A glass substrate formed of phase-separated glass in which spinodal phase separation is caused by heat treatment or the like, with part of its soluble parts being dissolved by acid treatment or the like, is preferable because the aforesaid characteristic pore diameter is easily formed in this glass substrate.

The filter for capturing minute substance preferably has heat resistance and chemical resistance. The filter high in such physical and chemical resistances can stably perform the separation and capturing operation even if heat treatment is performed in the separation operation, or even if the solution or suspension used is acid or alkaline.

[Method of Manufacturing Minute Substance Capturing Filter]

The filter for capturing minute substance of the present invention can be manufactured by, for example, a manufacturing method via phase-separated glass or a method of mechanically forming uniform and minute through holes. Hereinafter, the manufacturing method via the phase-separated glass will be described as one example.

The manufacturing method via the phase-separated glass can be performed by a phase-separation heat treatment step of phase-separating a glass plate as a material by heat treatment and a porosifying step of dissolving soluble parts of the phase-separated glass body by acid treatment or the like to make the glass plate porous. Hereafter, these steps will be described.

First, the glass plate as the material used here is not limited as long as it is formed of glass that phase-separates through spinodal decomposition. Examples of such glass include glasses having a composition of silicon oxide-boron oxide-alkali metal oxide, a composition of silicon oxide-boron oxide-alkali metal oxide, containing at least one kind of alkaline-earth metal oxide, zinc oxide, aluminum oxide, and zirconium oxide, a composition of silicon oxide-phosphate-alkali metal oxide, and a composition of silicon oxide-boron oxide-calcium oxide-magnesium oxide-aluminum oxide-titanium oxide.

More specifically, the examples include $SiO_2$—$B_2O_3$—$Na_2O$-based glass, $SiO_2$—$Al_2O_3$—$B_2O_3$—$Na_2O$-based glass, $SiO_2$—$Al_2O_3$—$B_2O_3$—$CaO$—$MgO$-based glass, $SiO_2$—$Al_2O_3$—$B_2O_3$—$Na_2O$—$K_2O$—$CaO$—$MgO$-based glass, $SiO_2$—$Al_2O_3$—$B_2O_3$—$Li_2O$—$Na_2O$—$MgO$-based glass, $SiO_2$—$Al_2O_3$—$B_2O_3$—$Li_2O$—$Na_2O$—$CaO$-based glass, $SiO_2$—$Al_2O_3$—$B_2O_3$—$Na_2O$—$K_2O$—$CaO$—$ZrO_2$-based glass, $SiO_2$—$B_2O_3$—$Na_2O$-based glass, and $SiO_2$—$B_2O_3$—$CaO$—$MgO$—$Al_2O_3$—$TiO_2$-based glass.

Among them, glass whose matrix composition is silicon oxide-boron oxide-alkali metal oxide is preferable, and the content of the silicon oxide in this glass is preferably 45 to 80 mol %, more preferably 50 to 80 mol %, still more preferably 55 to 80 mol %, and especially preferably 60 to 70 mol %.

The glass that phase-separates through the spinodal decomposition is glass having a phase-separation property. The phase separation property means that, taking borosilicate glass having silicon oxide-boron oxide-alkali metal oxide as an example, it is phase-separated into silicon oxide-rich phases and alkali metal oxide-boron oxide-rich phases in the glass by heat treatment.

Typically, the glass can be phase-separated by the heat treatment of the above-described glass. A condition of this heat treatment may be set so that a desired property is obtained because a formed phase separation state varies depending on its heating temperature and treatment time. As the heating temperature is higher and as the treatment time is longer, the phase separation state progresses more and as a result, porous glass having a larger pore diameter is obtained. A change of the heating temperature has a large influence on the progress of the phase separation, but a change of the treatment time has a small influence on the progress of the phase separation, and thus in order to obtain a desired pore diameter, it is desirable to adjust the heating temperature for deciding a rough range of the pore diameter and adjust the treatment time for precisely controlling the pore diameter. For example, it is preferable that the heating temperature is set within a range of 400 to 800° C., and the treatment time is set to about 10 minutes to 200 hours, further within a range of 10 minutes to 100 hours. This condition is preferable especially for the aforesaid borosilicate glass.

In manufacturing the glass, for glass that has been phase-separated at a stage of melt produced when the raw material is melted, the aforesaid individual phase separation treatment can be omitted since the heating at the time of the melting includes the phase-separation heat treatment.

Next, the glass having been phase-separated (phase-separated glass) is subjected to acid treatment, whereby the alkali metal oxide-boron oxide-rich phases being acid soluble components are brought into contact with an acid solution to be dissolved and removed. The acid solution used here is not limited as long as it can dissolve the aforesaid soluble components, and for example, may be hydrochloric acid, sulfuric acid, nitric acid, hydrofluoric acid, or organic acid such as acetic acid, or a combination of these, and among all, is preferably inorganic acid such as hydrochloric acid or nitric acid.

This acid solution is preferably an aqueous solution, and its acid concentration may be appropriately set to desired pH. In this acid treatment, the temperature of the solution is set to a range from room temperature to 100° C., and the treatment time is set to about 10 minutes to 200 hours, further, about 10 minutes to 150 hours. When the acid concentration is high or the temperature is high, the time taken for leaching can be short, but a crack or a warp of the glass due to the leaching more frequently occurs. To prevent this, treatment of adding inorganic salt such as ammonium salt or borax to the acid solution may be performed.

Further, the acid-treated glass may be subjected to cleaning treatment with at least one kind of an alkaline solution and hot water. This cleaning treatment is intended to dissolve and remove residues produced by the acid treatment. At this time, the silicon oxide is removed by hydrolysis or the like and the porosification is sometimes promoted, and thus, the cleaning treatment can also be used for adjusting a degree of the porosification. In particular, the alkaline solution is effective for adjusting the degree of the porosification, and the hot water is effective for dissolving and removing the residues. So, in a case where the alkaline solution treatment and the hot water treatment are both performed, the hot water treatment preferably comes after the alkaline solution treatment. The hot water treatment thus following the alkaline solution treatment effectively removes the residues after etching and can improve transmittance of the glass substrate.

Examples of the alkali used here include alkaline solutions of sodium hydroxide, potassium hydroxide, tetramethylammonium hydroxide, and ammonia, and an alkaline aqueous solution is preferable. In the cleaning treatment with the alkali, the alkali concentration of the alkaline solution may be appropriately set within a range of 0.01 to 2.0 mol/L (0.01 to 2.0 normality), in particular, within a range of 0.1 to 2.0 mol/L (0.1 to 2.0 normality). In this alkali treatment, the temperature of the solution is preferably 10 to 60° C., and the treatment time is preferably five minutes to ten hours, and especially preferably five minutes to two hours.

As the hot water, pure water or the like containing only a little impurity and heated to 50 to 90° C. is preferably used, and the treatment time is preferably five minutes to two hours.

Here, it suffices that only one of the treatment with the alkaline solution and the treatment with the hot water is performed, but the both may be performed. As a result of thus performing the cleaning treatment with at least one kind of the alkaline solution and the hot water after the acid treatment, the acid soluble parts formed by the phase separation through the spinodal decomposition are dissolved by the acid treatment to become holes, and continuous through holes in which these holes are connected with a substantially equal pore diameter from one main surface up to the other main surface are formed.

Depending on the treatment times of the acid treatment and the additional alkali and hot water treatments, the degree of the porosification in the glass body changes, and by performing these treatments for a long time, it is possible to adjust the diameter of the pores. Therefore, the treatment condition may be appropriately changed so that the pores with a desired diameter can be obtained.

Further, the strength of the glass plate varies depending on the phase-separation condition and the treatment times of the acid treatment and so on. The optimum phase-separation condition depends on the glass composition, and to find the optimum phase-separation condition, examining a T-T-T curve is effective, for instance. By making the phase separation progress in a temperature range, for example, about 100° C. lower than a temperature range where the phase separation most easily progresses, which range is found from the T-T-T curve, it is possible to make the pore diameter small. If the treatment time of the dissolving treatment such as the acid treatment is long, the strength also tends to become low. Accordingly, the phase separation condition and the treatment conditions of the acid treatment and so on may be appropriately changed so that the glass plate has strength high enough to be used for the separation of the minute substance in a solution. That is, the strength can be adjusted by adjusting the composition of the glass plate, the phase-separation heat treatment condition (temperature and time), and the porosification condition (liquid type, the liquid composition, the liquid concentration, the treatment temperature, the treatment time).

By, for example, forming a predetermined functional layer on the filter surface by applying a polymer or an inorganic film on the surface by dip coating, spin coating, sputtering, or ink jetting after the porosification, it is possible to impart other physical and chemical functions to the filter for capturing minute substance. Depending on the kind of the formed functional layer whose function is, for example, improving a hydrophile property of the surface to improve filtering performance, imparting adsorption specificity of capturing only a specific substance, or making the filter surface difficult to adsorb a specific substance, it is possible to obtain a glass substrate having a desired property.

In a case where the minute substance to be captured is an extracellular vesicle, the filter used is preferably a cell capturing filter having a covering layer formed of a protein anti-adhesion agent in view of preventing the extracellular vesicle from adhering to the filter and being incapable of peeling off. In forming the covering layer, the protein anti-adhesion agent may be applied as it is, or it may be dispersed in a medium such as a solvent or a dispersion medium and thereafter the medium may be removed. Here, as the protein anti-adhesion agent, a polymer having a constitutional unit having a bio-compatible group is usable. Specifically, a polymer whose constitutional unit is polyethylene glycol or 2-methacryloyloxyethyl phosphorylcholine is usable, and besides, a fluorine-containing polymer having a bio-compatible group described in WO2016/002796 is usable.

[Minute Substance Capturing Method]

Next, the minute substance capturing method using the filter for capturing minute substance of the present invention will be described.

The minute substance capturing method of the present invention is a method in which a minute substance with a 10 to 500 nm average particle diameter contained in a solution or a suspension is introduced to a glass substrate made of porous glass and the minute substance is separated and captured by the glass substrate.

Here, an average pore diameter of pores that the glass substrate in use has is within a range of 30 to 500% of the average particle diameter of the minute substance, and 90% or more of total pore volume of the pores have pore diameters within a range of 60 to 140% of a pore diameter at peak top in a pore diameter distribution of the pores.

At the time of the capturing, the solution or suspension containing the minute substance is supplied onto the aforesaid filter for capturing minute substance being a capturing means and is solid-liquid separated. As a result of the solid-liquid separation, liquid passes through the filter for capturing minute substance, that is, the liquid passes through the capturing means and is discharged from a lower portion of the capturing means. On the other hand, the minute substance which is a solid component cannot pass through the pores of the filter for capturing minute substance and is captured either on the surface or in the pores.

For the efficient solid-liquid separation at this time, the viscosity of the solution or suspension before the separation is preferably adjusted to $2 \times 10^{-3}$ Pa·s or less. A liquid component for thus adjusting the viscosity is, for example, water or alcohol.

In a case where a pressure is applied in the capturing, the pressure is preferably 0.1 to 100 MPa. Setting the pressure to 0.1 MPa or more enables to promote the solid-liquid separation, and setting the pressure to 100 MPa or less enables to prevent a breakage of the filter for capturing minute substance.

[Minute Substance Observation Glass Substrate]

The glass substrate for observing minute substance of the present invention is a plate-shaped glass substrate capable of separating and capturing a minute substance with a 10 to 500 nm average particle diameter contained in a solution or a suspension. The glass substrate for observing minute substance is made of porous glass having many pores in order to be capable of the solid-liquid separation of the minute substance and liquid.

As the glass substrate for observing minute substance, one suitable for surface observation on a filter is usable out of the above-described filters for capturing minute substance. Hereinafter, the glass substrate for observing minute substance will be described, but preferable forms of constituent features not specifically described out of the constituent features common to the filter for capturing minute substance are the same as those of the filter for capturing minute substance.

The average particle diameter of the minute substance to be observed in the present invention is 10 to 500 nm, and is preferably 50 to 150 nm. In the present specification, the average particle diameter of the minute substance is a 50% integrated value ($D_{50}$) found from a volume-based particle diameter distribution measured by a laser diffraction/scattering method or microscope observation. Examples of the minute substance include asbestos, carbon black, ink, colloidal particles, virus, and biomolecules such as albumin, antibody, and exosome.

The glass substrate for observing minute substance of the present invention is intended to separate and capture such a minute substance, and therefore is made of porous glass having many pores.

Here, the average pore diameter of the pores that the glass substrate for observing minute substance has is 5 to 550 nm, preferably 10 to 300 nm, still more preferably 20 to 200 nm, and especially preferably 50 to 150 nm. The average pore diameter here refers to a pore diameter at peak top determined based on a pore diameter distribution found by a BHJ method from a nitrogen adsorption isotherm by a gas adsorption method.

The average pore diameter is preferably within a range of 30 to 110% of the average particle diameter of the minute substance to be separated and captured (that is, its ratio to the average particle diameter of the minute substance as a reference (100%) is preferably within a range of 30 to 110%). This ratio is more preferably 50 to 110%, and still more preferably 60 to 110%. By setting the average pore diameter to 110% or less of the average particle diameter of the minute substance (to the average particle diameter or less), it is possible to surely capture the minute substance on the glass substrate and to perform the subsequent observation of the minute substance efficiently. Further, by setting the average pore diameter to more than 30% of the average particle diameter of the minute substance, it is possible to reduce a pressure loss to efficiently separate the minute substance because of the absence of an excessively small pore diameter. It is also possible to pass a substance whose average particle diameter is excessively smaller than that of the target minute substance and capture only the target minute substance.

The aforesaid average pore diameter is more preferably within a range of 30 to 100% of the average particle diameter of the minute substance to be separated and captured (that is, its ratio to the average particle diameter of the minute substance as a reference (100%) is preferably within a range of 30 to 100%). This ratio is more preferably 50 to 100%, and still more preferably 60 to 100%. By setting the average pore diameter to 100% or less of the average particles diameter of the minute substance (to the average particle diameter or less), it is possible to more surely capture the minute substance on the glass substrate to efficiently perform the subsequent observation of the minute substance.

90% or more of total pore volume of the pores in the glass substrate for observing minute substance have pore diameters within a range of 60 to 140% of the pore diameter at peak top in the pore diameter distribution (that is, ratios of their pore diameters to the pore diameter at peak top as a reference (100%) are within a range of 60 to 140%). In other words, their pore diameters fall within ±40% of the pore diameter at peak top as the reference (0%) (note that the reference used for calculating the ratio at this time is the pore diameter at peak top similarly to the above). Owing to the narrow distribution width of the pore diameter distribution, it is possible to separate and capture the minute substance stably and efficiently. More preferably, 95% or more of the aforesaid pores have pore diameter s within the range of 60 to 140% of the pore diameter at peak top in the pore diameter distribution.

A standard deviation of a surface pore diameter of the glass substrate for observing minute substance is preferably 60% or less of the average particle diameter of the minute substance (that is, 60% or less when the average particle diameter of the minute substance is set as 100%). The standard deviation is more preferably 50% or less, and still more preferably 40% or less. With the standard deviation being such, the substances to be captured are trapped at the same height, enabling good-condition observation with a later-described observing means.

Note that the standard deviation of the surface pore diameter is found by the following method.

Specifically, the surface of the glass substrate for observing minute substance is observed with a scanning electron microscope, and image data is obtained. Further, this image data is analyzed by image analysis software "Image J". Then, from the obtained analysis result, the surface average pore diameter and the standard deviation are calculated. In the image data analysis, binarization processing is performed, and a threshold value is set at this time by, for example, a discriminant analysis method, a Kittler method, a mode method, a P-tile method, or a 3σ method. For a glass substrate such as that of the present invention, the mode method or the Kittler method is preferable. In more detail, the method described in Examples can be used for the measurement.

The surface average pore diameter and the standard deviation measured by this method do not always agree with the aforesaid average pore diameter. This is because the average pore diameter is average information of the whole bulk by a gas adsorption method, while the surface average pore diameter obtained by this measuring method is obtained though the evaluation of only the pore diameter on the surface. For example, in a case where the porous glass is obtained by heat treatment and acid treatment, the treatments are always performed from the surface, and accordingly, as the treatments progress inward from the bulk surface, the pore diameter distribution varies slightly.

The glass substrate for observing minute substance preferably has small autofluorescence in order for the later-described observation of the minute substance to be performed easily and surely, and for example, 400 nm to 800 nm wavelength quantum conversion efficiency is preferably 5% or less, more preferably 3% or less, and especially preferably 1% or less. Note that the quantum conversion efficiency in the present specification is expressed by a ratio of the number of photons emitted from a sample as luminescence and the number of photons absorbed by the sample when the sample is irradiated with excitation light, and the number of the photons is measured by an integrating sphere method.

[Method of Manufacturing Minute Substance Observation Glass Substrate]

The glass substrate for observing minute substance of the present invention can be manufactured by the same method as the manufacturing method described in the filter for capturing minute substance.

In this embodiment, glass phase-separated and acid-treated is preferably subjected to both alkaline solution treatment and hot water treatment. At this time, the hot water treatment desirably comes after the alkaline solution treatment. Such hot water treatment following the alkaline solution treatment can effectively remove residues after etching to improve light transmittance of the glass substrate, and effectively reduces noise or the like at the time of the observation.

Next, the minute substance observation device and the minute substance observation method using the glass substrate for observing minute substance of the present invention will be described with reference to the drawing.

[Minute Substance Observation Device]

The minute substance observation device of the present invention includes: a capturing means including the above-described glass substrate for observing minute substance, as a filter which separates and captures a minute substance with a 10 to 500 nm average particle diameter contained in a solution or a suspensions; and an observing means with which the minute substance captured on the surface of the glass substrate for observing minute substance is observed.

The minute substance observation device will be described with reference to FIG. 1. The minute substance observation device 10 illustrated in FIG. 1 includes: a capturing means 11 including a glass substrate for observing minute substance 11a; and an optical microscope 12 with which a surface of the glass substrate for observing minute substance 11a is observed.

Here, the capturing means 11 includes the glass substrate for observing minute substance 11a as a solid-liquid separation filter as described above. Accordingly, for example, the solution or suspension containing the minute substance is supplied from above the capturing means 11 and when liquid passes through the capturing means 11 to be discharged from a lower portion of the capturing means 11, it is possible to capture the minute substance on the surface of the glass substrate for observing minute substance 11a.

Having a small pore diameter, the glass substrate for observing minute substance 11a does not easily allow the passage of the liquid if the solution or suspension is merely supplied onto the glass substrate, and for this reason, a pressure is usually applied at the time of the liquid passage. The pressure may be applied with a pump or the like from the supplied solution or suspension side, or by a centrifugal force given from a centrifugal separator or the like. However, if an amount of the solution is very small, or if the viscosity of the solution is equal to or lower than that of water, the solution can flow to the glass substrate only by the permeation by a capillary phenomenon.

The capturing means 11 is preferably formed of a cylindrical or tubular member formed of a material such as glass, resin, or rubber, with the glass substrate for observing minute substance 11a fixed therein, so as to supply the solution or suspension to one side of the minute observation glass substrate 11a as described above and so as to have space for storing the solution or suspension.

The observing means 12 is used for observing the surface of the glass substrate for observing minute substance 11a on which the minute substance is captured by the capturing means 11 and examining properties of the captured minute substance. Examples of the observing means 12 include an electron microscope and an optical microscope. In a case where the minute substance to be observed is labeled by being coated with a fluorescent dye or a fluorescent material, a fluorescence microscope is preferable. Especially in a case where the target minute substance is a biological substance, the fluorescence microscope is suitably used.

The observing means 12 is composed of: a substrate fixing stand 12b which fixes the glass substrate for observing minute substance 11a having captured the minute substance obtained on its surface by the filtering means 11; and an optical mechanism 12a with which the surface of the fixed glass substrate for observing minute substance 11a is observed.

In the above description, the example where the capturing means 11 has the single glass substrate for observing minute substance 11a is described, but another glass substrate for observing minute substance having a different average pore diameter may be provided, or a glass filter or a resin filter having a different average pore diameter, though not corresponding to the glass substrate for observing minute substance of the present invention, may be provided. Thus combining the filters different in pore diameter makes it possible to separate and capture particles with different diameters contained in the solution or suspension in stages.

[Minute Substance Observation Method]

The minute substance observation method of the present invention includes: a capturing step of solid-liquid separating a solution or a suspension containing a minute substance with a 10 to 500 nm average particle diameter by the above-described glass substrate for observing minute substance; and an observing step of observing the surface of the glass substrate for observing minute substance which has captured the minute substance in the capturing step.

Hereinafter, the minute substance observation method of the present invention will be described, taking a case where the minute substance observation device in FIG. 1 is used as an example.

In the capturing step, the solution or suspension containing the minute substance is introduced into the capturing means 11 and the solution or suspension is solid-liquid separated by the glass substrate for observing minute substance 11a. As a result of the solid-liquid separation, liquid passes through the glass substrate for observing minute substance 11a and is discharged from its lower portion. On the other hand, the minute substance which is a solid component cannot pass through the pores of the glass substrate for observing minute substance 11a but is captured on its surface or in the pores.

At this time, for the efficient solid-liquid separation, the viscosity of the solution or suspension before the separation is preferably adjusted to $2\times10^{-3}$ Pa·s or less. A liquid component for thus adjusting the viscosity is, for example, water or alcohol.

In a case where a pressure is applied to the capturing means 11 in the capturing step, the pressure is preferably 0.1 to 100 MPa. Setting the pressure to 0.1 MPa or more enables to promote the solid-liquid separation, and setting the pressure to 100 MPa or less enables to prevent a breakage of the glass substrate for observing minute substance 11.

The observing step is a step of observing the surface of the glass substrate for observing minute substance 11a on which the minute substance is captured in the capturing step and examining properties and so on of the captured minute substance. Before the observing step, the glass substrate for observing minute substance 11a is first removed from the capturing means 11, is moved to the observing means 12 as illustrated by the broken line in FIG. 1, and is fixed on the substrate fixing stand 12b. Then, the fixed glass substrate for observing minute substance 11a is observed with the optical mechanism 12a, whereby information about the properties is obtained.

EXAMPLES

Hereinafter, the present invention will be specifically described by means of Examples, but the present invention is not limited at all by the description. Note that examples 1 to 4, 6 to 8 are Examples, and an example 5 is a comparative example.

Example 1

Particles of $SiO_2$, $B_2O_3$, and $Na_2CO_3$ as raw materials were mixed into a three-component composition of 65% $SiO_2$, 27% $B_2O_3$, and 0.8% $Na_2$ ($SiO_2$—$B_2O_3$—$Na_2O$) in molar percentage in terms of oxide, whereby a 900 g glass raw material was obtained.

This glass raw material was put into a platinum crucible and was heated to 1500° C. by a resistance-heating electric furnace to be melted. After four-hour deaeration and homogenization, the obtained molten glass was poured into a mold and was cooled from a temperature of [glass transition point (Tg: 486° C.)+50° C.] to room temperature at a 30° C./minute rate, whereby a glass block was obtained.

The glass block was heat-treated at 600° C. for three hours to be phase-separated. The phase-separated glass block was cut, polished, and finally mirror-finished on both surfaces, whereby two kinds of plate-shaped glasses, namely, a plate-shaped glass with a 7 mm$\phi$ diameter and a 0.5 mm thickness and a plate-shaped glass with a 7 mm$\phi$ diameter and a 1.0 mm thickness were obtained.

Next, these plate-shaped glasses were immersed in 1N $HNO_3$ for sixteen hours for leaching, and thereafter were cleaned with 1N NaOH and 60° C. hot water, whereby a glass substrate 1A (0.5 mm thick) and a glass substrate 1B (1.0 mm thick) for minute substance observation were obtained.

Regarding the obtained glass substrates, Table 1 shows the kind of a filter and phase-separation conditions (heat treatment temperature, heat treatment time), and in addition, show examined characteristics, that is, average pore diameter, distribution width in the pore diameter distribution, standard deviation of the surface pore diameter, plate thickness, the area of a main surface, (area/plate thickness/$Log_{10}$ (average pore diameter (nm)), 50 nm bead capture ratio, 100 nm bead capture ratio, 350 nm bead capture ratio. Here, as for the pore diameter distribution width, the pore diameter at peak top is defined as 0%.

Test Example 1

[Measurement of Bead Capture Ratio]

Dispersion solutions in which fluorescent beads with a 50 nm average particle diameter and with a 350 nm average particle diameter were dispersed in water were prepared. Next, the obtained glass substrates were each fixed in a cylindrical tube so as to tightly close the inside, whereby capturing means each capable of treating a 500 µL, dispersion solution were fabricated.

500 µL of each of the aforesaid prepared dispersion solutions was stored in each of these capturing means and subjected to ten-minute centrifugal separation under 10000 G (1.3 MPa pressure) by a centrifugal separator. Thereafter, fluorescence intensities of filtrates were measured with a plate reader, and the capture ratios of the respective fluorescent beads were calculated. Table 1 also shows the results.

When the glass substrates were taken out from the aforesaid capturing means obtained in the test example 1 and the glass substrate surfaces were observed with a fluorescence microscope, the captured fluorescent beads were confirmed on all the glass substrates.

Example 2 to Example 4

Glass substrates for observing minute substance were obtained by the same operation as that of the example 1 except that the phase-separation condition (heat treatment temperature) was set to that shown in Table 1. The obtained glass substrates are named glass substrates 2A to 3A (0.5 mm thick) and glass substrates 2B to 4B (1.0 mm thick).

Example 5

As the comparative example, a commercially available resin filter was prepared. As the resin filter of the example 5, a bottom filter out of two kinds of filters used in ExoMir (manufactured by COSMO BIO Co., Ltd., brand name) was used, and its characteristics were evaluated.

Further, a capturing means having only the filter used in the evaluation of the resin filter in ExoMir (having one kind of filter) was fabricated.

Liquid was completely passed through this capturing means using an attached manual pump. A fluorescence intensity of a filtrate was measured with a plate reader, and a capture ratio of fluorescent beads was calculated. Table 1 also shows the result. Since this resin filter has a week strength and its surface is not smooth, the observation with the fluorescence microscope was difficult.

Example 6 to Example 8

The glass block obtained in the example 1 was heat-treated at a predetermined temperature and for a predetermined time described in Table 2 to be phase-separated. The phase-separated glass block was cut, polished, and finally mirror-finished on both surfaces, whereby 5 mm×20 mm plate-shaped glasses with a 0.1 mm thickness, a 0.5 mm thickness, and a 1 mm thickness were obtained.

Next, these plate-shaped glasses were immersed in 1N $HNO_3$ for sixteen hours for leaching, and were thereafter cleaned with 1N NaOH and 60° C. hot water, whereby a glass substrate C (0.1 mm thick), a glass substrate D (0.5 mm thick), and a glass substrate E (1.0 mm thick) were obtained.

Out of the obtained glass substrates, regarding the 1.0 mm thick glass substrate 1E phase-separated at 600° C. (example 6), the 0.5 mm thick glass substrate 3D and the 1.0 mm thick glass substrate 3E phase-separated at 700° C. (example 7), and the 0.1 mm thick glass substrate 1C phase-separated at 600° C. (example 8), Table 2 shows the kind of a filter, phase-separation conditions (heat treatment temperature, heat treatment time), and in addition, shows examined characteristics, that is, average pore diameter, plate thickness, the area of a main surface, and (area/plate thickness/$Log_{10}$ (average pore diameter (nm)). When three-point bending strengths of these were further measured, it was found out that the strength was high in a glass substrate in which the ratio between the ratio of the area of the main surface to the plate thickness and the average pore diameter (area ($cm^2$)/plate thickness (mm)/$Log_{10}$ (average pore diameter (nm))) was 4.5 $cm^2$/mm or less.

Test Example 2

[Measurement of Three-Point Bending Strength]

Three-point bending strength was measured on ten samples according to JIS R 1601:2008, using TENSILON UTA-5kN (manufactured by ORIENTEC Co., Ltd., brand name).

TABLE 1

|  |  | Example 1 | | Example 2 | |
| --- | --- | --- | --- | --- | --- |
| | Kind of filter | Substrate 1A | Substrate 1B | Substrate 2A | Substrate 2B |
| Phase-separation conditions | Heat treatment temperature (° C.) | 600 | | 650 | |
| | Heat treatment time (hours) | 3 | | 3 | |
| Substrate characteristics | Average pore diameter (nm) | 38 | | 120 | |
| | Distribution width in pore diameter distribution | Within ±40% | | Within ±40% | |
| | Standard deviation of surface pore diameter (nm) | 16 | | 53 | |
| | Plate thickness (mm) | 0.5 | 1.0 | 0.5 | 1.0 |
| | Area (cm$^2$) | 0.385 | | 0.385 | |
| | (Area/plate thickness/Log10 pore diameter) | 0.5 | 0.2 | 0.4 | 0.2 |
| | 50 nm bead capture ratio (%) | 99< | 99< | — | — |
| | 100 nm bead capture ratio (%) | — | — | — | — |
| | 350 nm bead capture ratio (%) | — | — | — | — |

|  |  | Example 3 | | Example 4 | Example 5 |
| --- | --- | --- | --- | --- | --- |
| | Kind of filter | Substrate 3A | Substrate 3B | Substrate 4B | Resin filter |
| Phase-separation conditions | Heat treatment temperature (° C.) | 700 | | 700 | — |
| | Heat treatment time (hours) | 3 | | 24 | — |
| Substrate characteristics | Average pore diameter (nm) | 180 | | 290 | 20 |
| | Distribution width in pore diameter distribution | Within ±40% | | Within ±40% | Within ±50% |
| | Standard deviation of surface pore diameter (nm) | 78 | | 47 | 337 |
| | Plate thickness (mm) | 0.5 | 1.0 | 1.0 | 0.1 |
| | Area (cm$^2$) | 0.385 | | 0.385 | 4.91 |
| | (Area/plate thickness/Log10 pore diameter) | 0.3 | 0.2 | 0.2 | 37.7 |
| | 50 nm bead capture ratio (%) | — | — | — | 15 |
| | 100 nm bead capture ratio (%) | — | 94 | 95 | — |
| | 350 nm bead capture ratio (%) | — | 96 | 91 | 15 |

TABLE 2

|  |  | Example 6 | Example 7 | | Example 8 |
| --- | --- | --- | --- | --- | --- |
| | Kind of filter | Substrate 1E | Substrate 3D | Substrate 3E | Substrate 1C |
| Phase-separation conditions | Heat treatment temperature (° C.) | 600 | 700 | | 600 |
| | Heat treatment time (hours) | 3 | 3 | | 3 |
| Substrate characteristics | Average pore diameter (nm) | 38 | 180 | | 38 |
| | Plate thickness (mm) | 1.0 | 0.5 | | 1.0 | 0.1 |
| | Area (cm$^2$) | 0.75 | 0.75 | | 0.75 |
| | (Area/plate thickness/Log10 pore diameter) | 0.5 | 0.7 | 0.3 | 4.7 |
| | Three-point bending strength (N) | 24.3 | 12.2 | 33.4 | 0.2 |

(Average Pore Size, Pore Size Distribution)

The pore diameter distribution was found by a BHJ method from a nitrogen adsorption isotherm by a gas adsorption method. The average pore diameter refers to a peak top pore diameter determined based on the above obtained pore diameter distribution. The distribution width of the pore diameter distribution is expressed as a ratio to the peak top pore diameter defined as a reference (100%).

[Standard Deviation of Surface Pore Size]

The standard deviation of the surface pore diameter was measured as follows. The surfaces of the samples were observed with a scanning electron microscope and image data were obtained. Further, the image data were subjected to image processing by image analysis software "Image J" and were analyzed.

Image Processing

First, images obtained by the scanning electron microscope (SEM) observation were binarized using the image analysis software (open source of National Institutes of Health [NIH] in USA, name "Image J")

Since the glass structures were displayed being highlighted on the SEM images, brightness and darkness were first reversed in the binarization to make the glass structures displayed dark. Thereafter, brightness and contrast were corrected so as to make the glass structures conspicuous, and only the glass structures were selected by setting a threshold value, whereby binarized images were obtained. As a method to set the threshold value, a Kittler method was used.

Image Analysis

Next, horizontal lines were drawn so as to cross the obtained binarized images and glass-to-glass distances on the lines, that is, pore widths were measured. At least five horizontal lines or more were drawn per one image and fifty points or more were set as measurement points. Since the glasses of this example have a random structure due to the nature of the spinodal phase separation, the area displayed in each image may differ. However, in this method, the analysis was indiscriminately performed by the above-described operation irrespective of their shapes.

From the pore widths found by the image analysis under the condition set as described above, the surface average pore diameter and the standard deviation were calculated.

As described above, the glass substrate for observing minute substance of the present invention is capable of surely capturing the minute substance with a 10 to 500 nm average particle diameter contained in a liquid or a suspension. In the solid-liquid separation of such a minute substance, it is required not to unnecessarily increase a pressure loss in order to pass the liquid, and the glass substrate of the present invention has been found to be good in these characteristics. Further, the minute substance observation device and observation method using the glass substrate for observing minute substance enable the observation of the captured minute substance as it is, which enables the efficient observation, inspection, and the like of the minute substance.

The glass substrate for observing minute substance of the present invention is a glass substrate for observing minute substance enabling the capturing and observation of a minute substance and is suitable for the capturing and observation of a minute substance. Further, the glass substrate for observing minute substance is usable also for capturing a substance having a larger particle diameter than that of the minute substance.

What is claimed is:

1. A filter for capturing a minute substance, comprising a porous glass substrate having a plurality of pores, wherein
the porous glass substrate comprises phase-separated glass formed through a spinodal decomposition,
the plurality of pores has an average pore diameter ranging from 5 to 2500 nm and a pore diameter ranging from 60 to 140% of a pore diameter corresponding to a maximum value in a pore diameter distribution of the plurality of pores occupies 90% or more of total pore volume of the plurality of pores, and
the porous glass substrate satisfies the following formula (1):

$$\frac{S}{D \cdot \log_{10} d} \leq 4.5 [\text{cm}^2/\text{mm}] \quad (1)$$

wherein S [cm$^2$] is an area of main surface of the glass substrate,
D [mm] is a plate thickness of the porous glass substrate, and
d [nm] is the average pore diameter.

2. The filter for capturing a minute substance according to claim 1, wherein the porous glass substrate has a porosity ranging from 20 to 90%.

3. A filter for capturing a minute substance, comprising a porous glass substrate having a plurality of pores, wherein
the plurality of pores has an average pore diameter ranging from 5 to 2500 nm and a pore diameter ranging from 60 to 140% of a pore diameter corresponding to a maximum value in a pore diameter distribution of the plurality of pores occupies 90% or more of total pore volume of the plurality of pores, and
the porous glass substrate has a covering layer on a surface, the covering layer comprising a protein anti-adhesion agent.

4. A minute substance observation device comprising:
a capturing unit including the filter according to claim 1 and being capable of separating and capturing a minute substance with an average particle diameter of 10 to 500 nm contained in a solution or a suspension; and
an observing unit for observing the minute substance captured on a surface of the glass substrate.

5. The minute substance observation device according to claim 4, wherein the observing unit is a fluorescence microscope.

6. A minute substance capturing method comprising:
introducing a solution or a suspension comprising a minute substance with a 10 to 500 nm average particle diameter to a porous glass substrate having a plurality of pores; and
separating and capturing the minute substance by the glass substrate,
wherein
the porous glass substrate comprises phase-separated glass formed through a spinodal decomposition,
the plurality of pores has an average pore diameter ranging from 30 to 500% of the average particle diameter of the minute substance, and a pore diameter ranging from 60 to 140% of a pore diameter corresponding to a maximum value in a pore diameter distribution of the plurality of pores occupies 90% or more of total pore volume of the plurality of pores.

7. The minute substance capturing method according to claim 6, wherein the porous glass substrate satisfies the following formula (1):

$$\frac{S}{D \cdot \log_{10} d} \leq 4.5 [\text{cm}^2/\text{mm}], \quad (1)$$

wherein
S [cm$^2$] is an area of main surface of the glass substrate,
D [mm] is a plate thickness of the porous glass substrate, and
d [nm] is the average pore diameter.

8. A minute substance observation method comprising:
introducing a solution or a suspension comprising a minute substance with a 10 to 500 nm average particle diameter to a porous glass substrate having a plurality of pores;
separating and capturing the minute substance by the glass substrate; and
observing the minute substance captured by the glass substrate,
wherein
an average pore diameter ranging from 30 to 110% of the average particle diameter of the minute substance,
each of the plurality of pores has a surface pore diameter on a main surface of the porous glass substrate, and a standard deviation of the surface pore diameter on an uppermost surface of the glass substrate is 60% or less of the average particle diameter of the minute substance, and
a pore with a pore diameter ranging from 60 to 140% of a pore diameter corresponding to a maximum value in a pore diameter distribution of the plurality of pores occupies 90% or more of total pore volume of the plurality of pores.

9. The minute substance observation method according to claim 8, wherein the average pore diameter is ranging from 30 to 100% of the average particle diameter of the minute substance.

10. A minute substance observation method comprising:
separating and capturing a minute substance with a 10 to 500 nm average particle diameter by the filter according to claim 1, from a solution or a suspension comprising the minute substance; and observing the minute substance captured on a surface of the glass substrate for observing minute substance.

11. The minute substance observation method according to claim 8, wherein a fluorescence microscope is used for the observation.

* * * * *